United States Patent

Luebbe et al.

[11] Patent Number: 5,902,572
[45] Date of Patent: May 11, 1999

[54] ANHYDROUS GEL DEODORANT COMPOSITIONS

[75] Inventors: John Paul Luebbe, Lawrenceburg, Ind.; Li Li; Curtis Bobby Motley, both of West Chester, Ohio; David Frederick Swaile, Cincinnati, Ohio; Gerald John Guskey; Thomas Vincent Orr, both of Cincinnati, Ohio

[73] Assignee: Procter & Gamble Company, Cincinnati, Ohio

[21] Appl. No.: 09/071,106

[22] Filed: May 1, 1998

Related U.S. Application Data

[63] Continuation-in-part of application No. 08/880,939, Jun. 23, 1997.

[51] Int. Cl.[6] .................................................. A61K 7/34
[52] U.S. Cl. .................................. 424/66; 424/65; 424/68
[58] Field of Search .................................. 424/66, 65, 68

[56] References Cited

U.S. PATENT DOCUMENTS

| | | | |
|---|---|---|---|
| 5,429,816 | 7/1995 | Hofrichter et al. | 424/66 |
| 5,591,424 | 1/1997 | Hofrichter et al. | 424/66 |
| 5,650,144 | 7/1997 | Hofrichter et al. | 424/66 |

*Primary Examiner*—José G. Dees
*Assistant Examiner*—Michael A. Williamson
*Attorney, Agent, or Firm*—William J. Winter; Tara M. Rosnell; David L. Suter

[57] ABSTRACT

Disclosed are anhydrous gel deodorant compositions comprising from about 0.001% to about 50% by weight of deodorant active, fragrance, or combination thereof, from about 0.01% to about 20% by weight of a gellant; from about 1% to about 50% by weight of a nonpolar volatile solvent having a solubility parameter of less than 8.0 $(cal/cm^3)^{0.5}$, a vapor pressure of from about 0.01 mm Hg to about 6 mm Hg at 25° C., and a boiling point at 1 atm of less than about 250° C.; from about 1% to about 15% by weight of a polar solvent having a solubility parameter of from 12.5 $(cal/cm^3)^{0.5}$ to about 25 $(cal/cm^3)^{0.5}$ and optionally a moderately polar solvent having a solubility parameter of from about 8.0 $(cal/cm^3)^{0.5}$ to less than 12.5 $(cal/cm^3)^{0.5}$, preferably 1,2-hexanediol. Other preferred embodiments include those which contain combinations of triclosan and triclocarban for improved deodorant efficacy. These compositions provide improved performance and skin feel characteristics, and are especially effective at providing deodorant application which is milder to the skin, and improved product clarity.

26 Claims, No Drawings

ANHYDROUS GEL DEODORANT COMPOSITIONS

This application is a cip of Ser. No. 08/880,939, filed Jun. 23, 1997.

FIELD OF INVENTION

This invention relates to anhydrous gel deodorant compositions containing a nonpolar volatile solvent in combination with a polar solvent, gellant, and deodorant active or fragrance. These compositions are milder to the skin and cause less skin irritation, and have good skin feel characteristics during and after application.

BACKGROUND OF THE INVENTION

Human body malodors are generally believed to be caused in part by microbial interaction with sweat gland secretions which produces pungent fatty acids. Aside from cleansing, one way such odors are controlled is by the topical application to the underarm of an antiperspirant or deodorant composition.

Deodorant compositions in gel form are especially popular as a means for preventing or masking malodor arising from perspiration. These gel deodorants compositions are typically in the form of a solid or soft solid stick and, like other antiperspirant or deodorant products, are also applied topically to the underarm or other area of the skin. The gel deodorants, however, typically glide onto the skin more easily than many other antiperspirant or deodorant products, and leave little if any visible residue after application. These gel deodorants typically contain a gellant, a polar solvent to solubilize the gellant, and a deodorant active such as an antimicrobial active, perfume or other odor masking material. Commonly used gellants in such systems include fatty acid salts, examples of which include sodium or potassium salts of $C_{12}$–$C_{22}$ fatty acids. Polar solvents commonly used in combination with the fatty acid salts to form the gel structure of the composition include monohydric or dihydric alcohols, especially ethanol and glycols such as propylene glycol, dipropylene glycol and other higher molecular weight polypropylene glycols. Many of these gel deodorants, however, are not mild to the skin and can cause an excessive skin irritation.

It is therefore an object of the present invention to provide an anhydrous gel deodorant composition that is milder to the skin and causes less skin irritation, and further to provide such a composition that also has good skin feel characteristics during and after topical application. It is yet another object of the present invention to provide such a composition wherein the composition comprises a nonpolar volatile solvent in combination with a polar solvent, and further to provide such a composition which optionally comprises a moderately polar solvent.

SUMMARY OF THE INVENTION

The present invention is directed to anhydrous gel deodorant compositions comprising from about 0.001% to about 50% by weight of deodorant active, fragrance, or combination thereof; from about 0.01% to about 20% by weight of a gellant; from about 3% to about 50% by weight of a nonpolar volatile solvent having a solubility parameter of less than 8.0 $(cal/cm^3)^{0.5}$ and a vapor pressure of from about 0.01 mm Hg to about 6 mm Hg at 25° C.; from about 1% to about 15% by weight of a polar solvent having a solubility parameter of from 12.5 $(cal/cm^3)^{0.5}$ to about 25 $(cal/cm^3)^{0.5}$ and optionally a moderately polar solvent having a solubility parameter of from 8.0 $(cal/cm^3)^{0.5}$ to less than 12.5 $(cal/cm^3)^{0.5}$ that these anhydrous gel deodorant compositions provide improved performance and skin feel characteristics, and are especially effective at providing deodorant application which is milder to the skin and which causes little or no skin irritation.

DETAILED DESCRIPTION

The anhydrous gel deodorant compositions of the present invention comprise as essential ingredients a gellant, a volatile nonpolar solvent, a polar solvent and a perfume or deodorant active. These anhydrous gel deodorant compositions are intended for topical application to the underarm or other suitable areas of the skin. The compositions are preferably in the form of solid or soft solid sticks, but can also be formulated in a variety of non-stick formulations suitable for application to the underarm or other area of the skin.

The term "anhydrous" as used herein refers to the gel deodorant composition of the present invention, and means that the composition is substantially free of water, preferably less than about 5%, more preferably less than about 1%, most preferably zero percent, by weight of free or added water in the gel deodorant.

The term "ambient conditions" as used herein refers to surrounding conditions under about one atmosphere of pressure, at about 50% relative humidity, and at about 25° C.

The term "substantially free of aromatic hydrocarbons" as used herein refers to the anhydrous gel deodorant compositions of the present invention which contain less than about 10%, preferably less than about 5%, by weight of aromatic hydrocarbons selected from the group of α-pinene, β-pinene, d-limonene and other terpenes.

The anhydrous gel deodorant compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the active level and, therefore, do not include solvents or by-products that may be included in commercially available materials, unless otherwise specified.

Deodorant Active and Fragrance

The anhydrous gel deodorant compositions of the present invention comprise a deodorant active, fragrance or combination thereof, which includes deo-fragrances, at concentrations ranging from about 0.001% to about 50%, preferably from about 0.01% to about 20%, more preferably from about 0.1% to about 10%, by weight of the composition. These deodorant actives and perfumes include any known or otherwise safe and effective deodorant or fragrance suitable for topical application to human skin.

Unless otherwise specified, the term "active" as used herein refers generally to deodorant actives or fragrances, whereas the term "deodorant active" specifically refers to topical materials which can prevent or eliminate malodors resulting from perspiration. The term "fragrance" as used herein specifically refers to any topical material which covers or masks malodors resulting from perspiration, or which otherwise provides the composition with the desired perfumed aroma.

A) Deodorant active

Deodorant actives suitable for use in the anhydrous gel deodorant composition includes any topical material that is known for or is otherwise effective in preventing or eliminating malodor associated with perspiration. These deodorant actives are typically antimicrobial agents (e.g., bacteriocides, fungicides), malodor-absorbing material, or combinations thereof.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Preferred deodorant actives are triclosan, triclocarban and combinations thereof, wherein the preferred concentration of either triclosan or triclocarban ranges from about 0.01% to about 1.0%, more preferably from about 0.1% to about 0.5%, even more preferably from about 0.1% to about 0.3%, by weight of the composition, and wherein the total concentration of triclosan and triclocarban when used together in a composition ranges from about 0.01% to about 2.0%, more preferably from about 0.2% to about 1.0%, even more preferably from about 0.2% to about 0.6%, by weight of the composition. It has been found that the combination of these two deodorant actives provides a deodorant efficacy that exceeds the cumulative deodorant efficacy that one would otherwise predict from such a combination.

The preferred combination of triclosan and triclocarban is effective in providing improved deodorant performance from the deodorant compositions described herein, or from any known deodorant or topical composition containing such a combination that is otherwise suitable for application to human skin. The present invention is therefore also directed to a method of controlling malodor associated with human perspiration by topically applying the triclosan/triclocarban combination described above, or any other suitable composition containing the triclosan/triclocarban combination described above, to the underarm or other area of the skin. From most deodorant compositions containing this combination, from about 0.1 gram to about 2.0 gram per axilla of the deodorant composition is applied, preferably once or twice daily, more preferably once daily.

Other deodorant actives include odor-absorbing materials such as carbonate and bicarbonate salts, including alkali metal carbonates and bicarbonates, ammonium and tetraalkylammonium Preferred are sodium and potassium salts of such odor-absorbing materials.

The anhydrous gel deodorant composition is preferably substantially free of astringent antiperspirant actives such as aluminum or zirconium astringent salts or complexes. In this context, the term "substantially free" means that the gel deodorant composition preferably contains less than about 5%, more preferably less than about 2%, most preferably zero percent, by weight of such astringent antiperspirant actives.

B) Fragrance

Fragrances suitable for use in the anhydrous gel deodorant composition include any topical material that is known for or is otherwise effective in masking malodor associated with perspiration, or which otherwise provides the composition with the desired perfumed aroma. These fragrances include any perfume or perfume chemical suitable for topical application to the skin.

The concentration of the fragrance in the anhydrous gel deodorant composition should be effective to provide the desired aroma characteristics or to mask malodor, wherein the malodor is inherently associated with the composition itself or is associated with malodor development from human perspiration. Also, the fragrance and whatever carriers accompany it should not impart excessive stinging to the skin, especially broken or irritated skin, at the levels previously disclosed. The fragrance will typically be in the form of water insoluble perfumes that are solubilized in the anhydrous gel deodorant composition.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and P-naphthyl methyl ether); esters (such as diethyl phthalate, phenylethyl phenylacetate, non-anolide-114). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, parahydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable fragrances are those which mask or help to mask odors associated with perspiration (hereinafter referred to as odor masking fragrances), some nonlimiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The fragrance for use herein may also contain solubilizers, diluents, or solvents which are well known in the art. Such materials are described in Arctander, Perfume and Flavour Chemicals (Aroma Chemicals), Vol. I and II (1969). These materials typically include dipropylene glycol, diethylene glycol, $C_1$–$C_6$ alcohols, and benzyl alcohol.

Gellant

The anhydrous gel deodorant composition of the present invention comprises a gellant suitable for providing the desired hardness and application characteristics to the composition. Gellant concentrations range from about 0.01% to about 20%, preferably from about 0.1% to about 10%, more preferably from about 1% to about 8%, even more preferably from about 3% to about 7%, by weight of the anhydrous gel deodorant composition.

Any known gellant or gellant system may be used in the anhydrous gel deodorant composition of the present invention provided that the selected gellants can melt and form a solution or other homogenous liquid or liquid dispersion with the selected solvent system described herein at a processing temperature of from about 50° C. to about 150° C., preferably from about 50° C. to about 120° C., more preferably 60° C. to about 100° C. The selected gellant must also provide the gel deodorant composition with the desired gel matrix after formulation and completion of processing which then provides the composition with the desired hardness or spreading characteristics.

Preferred gellants for use in the anhydrous gel deodorant composition of the present invention are salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, sodium laurate, sodium arachidate, sodium behenate, potassium stearate, potassium palmitate, sodium myristate, aluminum monostearate, and combinations thereof. Most preferred is sodium stearate.

Non-limiting examples of fatty acids suitable for making the fatty acid gellants include acids such as myristic, palmitic, stearic, oleic, lauric, arachidic, behenic, linoleic, linolenic, margaric and combinations thereof. These fatty acids are preferably derived from sources such as coconut oil, beef tallow, lanolin, fish oil, beeswax, palm oil, peanut oil, olive oil, cottonseed oil, soybean oil, corn oil, rapeseed oil, rosin acids, greases, and other natural sources, or are derived by synthetic or semisynthetic methods well known to those skilled in the formulation art.

Other suitable gellants suitable for use in the anhydrous gel deodorant composition include hydroxy acids, fatty acids, esters and amides of fatty acids and fatty acid salts, hydroxy fatty acids, cholesterolic materials, lanolinolic materials, and other amide gellants known for use as gelling agents or which are otherwise described in detail hereinafter.

Nonlimiting examples of suitable fatty acid gellants include fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, combinations thereof, and salts thereof.

Other nonlimiting examples of specific gellants suitable for use in the anhydrous gel deodorant composition include those which correspond to the following formula:

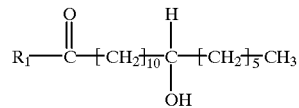

wherein $R_1$ is $OR_2$ or $NR_2R_3$; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

Nonlimiting examples of suitable amide gellants for use in the anhydrous gel deodorant composition include disubstituted or branched monoamide gellants, monosubstituted or branched diamide gellants, triamide gellants, and combinations thereof. Preferred are alkyl amides of di- and/or tri-basic carboxylic acids or anhydrides which conform to the formula:

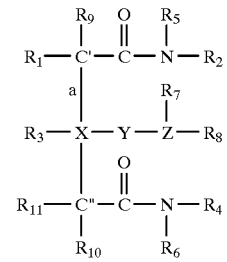

wherein a backbone is formed from the linkage of C', C" and X and wherein
  a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_2$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–C18 alkoxy, $C_{12}$–$C_{18}$ alkyl esters, $C_{12}$–$C_{18}$ alkyl ethers, or $C_{12}$–$C_{18}$ alkyl substituted aryl;
  b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C$ alkyl ethers, preferably a $C_1$ $C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nil, nitrogen, aryl or $-(CH_2)_n-$ where n is an integer from 1 to 6, preferably $-(CH_2)_n-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
   (i) when X is nil, Y, Z, $R_3$, $R_7$ and $R_8$ are nil, C' is bonded directly to C''' and $R_1$ is not a hydrogen;
   (ii) when X and Z are not nil and Y is nil, X is directly bonded to Z;
   (iii) when Z is nil, a hydrogen or a hydroxy, $R_7$ and $R_8$ are nil; and
   (iv) when "a" is a double bond, $R_3$ and $R_8$ are nil.

Nonlimiting examples of specific alkyl amide gellants suitable for use in the anhydrous gel deodorant composition include alkyl amides of citric acid, tricarbalkylic acid, aconitic acid, nitrilotriacetic acid, succinic acid and itaconic acid such as 1,2,3-propane tributylamide, 2-hydroxy-1,2,3-propane tributylamide, 1-propene-1,2,3-trioctylamide, N,N', N"-tri(acetodecylamide)amine, 2-dodecyl-N,N'-dihexylsuccinamide, and 2-dodecyl-N,N'-dibutylsuccinamide.

Volatile Nonpolar Solvent

The anhydrous gel deodorant compositions of the present invention comprise a volatile nonpolar solvent having a select vapor pressure and solubility parameter. Concentration of the volatile nonpolar solvent in the anhydrous gel deodorant composition ranges from about 1% to about 50%, preferably from about 10% to about 40%, more preferably from 20% to about 40%, even more preferably from about 30% to about 40%, by weight of the composition.

The term "volatile" as used herein refers to the volatile nonpolar solvent of the anhydrous gel deodorant composition of the present invention, and in this context specifically refers to nonpolar solvents having a vapor pressure as measured at 25° C. of from about 0.01 mmHg to about 6 mmHg, preferably from about 0.02 mmHg to about 1.5 mmHg, and an average boiling point at one atmosphere of pressure (1 atm) of less than about 250° C., preferably less than about 235° C., at 1 atmosphere (atm) of pressure.

The term "nonpolar" as used herein refers to the volatile nonpolar solvent of the anhydrous gel deodorant composition of the present invention, and in this context specifically refers to volatile solvents having a solubility parameter of less than 8.0 $(cal/cm^3)^{0.5}$, preferably from about 5.0 $(cal/cm^3)^{0.5}$ to less than 8.0 $(cal/cm^3)^{0.5}$, more preferably from 6.0 $(cal/cm^3)^{0.5}$ to about 7.60 $(cal/cm^3)^{0.5}$.

Solubility parameters for the volatile nonpolar solvent and other materials described herein are determined by methods well known in the chemical arts for establishing the relative polar character of a solvent or other material. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Volatile nonpolar solvents suitable for use in the anhydrous gel deodorant compositions are those solvents having the above-described vapor pressure and solubility parameters, which can also include hydrocarbons, esters, amides, and ethers having the requisite vapor pressure and solubility parameter, Preferred are nonpolar hydrocarbon solvents which can be cyclic, branched or chain configurations, most preferably branched chain hydrocarbons.

The volatile nonpolar solvent is most preferably a branched chain hydrocarbon having the requisite vapor pressure and solubility parameter and having from about 4 to about 30 carbon atoms, preferably from about 4 to about 20 carbon atoms, more preferably from about 6 to about 20 carbon atoms. The anhydrous gel deodorant composition most preferably comprises a combination of two or more of the above-described branched chain hydrocarbons, wherein the combination of two or more hydrocarbons have different molecular weights, number of carbon atoms, and/or chain configurations. Specific nonlimiting examples of these most preferred combination of hydrocarbon solvents include the isoparaffins available from Exxon Chemical Company, Baytown, Tex. U.S.A, as Isopar M (C13–C14 isoparaffin), Isopar C (C7–C8 Isoparaffin), C8–C9 Isoparaffin (Isopar E), Isopar G (C10–11 Isoparaffin), Isopar L (C11–C13 Isoparaffin) and Isopar H (C11–C12 Isoparaffin). Other nonlimiting examples of suitable branched chain hydrocarbons include Permethyl 99A (isododecane), Permethyl 102A (isoeicosane), Permethyl 101A (isohexadecane), and combinations thereof. The Permethyl series are available from Preperse, Inc., South Plainfield, N.J. U.S.A. Other nonlimiting examples of suitable branched chain hydrocarbons include petroleum distillates such as those available from Phillips Chemical as Soltrol 130, Soltrol 170, and those available from Shell as Shell Sol 70, –71, and –2033.

Nonlimiting examples of other suitable nonpolar volatile solvents for use in the anhydrous gel deodorant composition include dibutyl adipate, diisopropyladipate, dodecane, octane, decane and combinations thereof. Yet another example includes C11–C15 alkanes/cycloalkanes available from Exxon as Exxsol D80.

Polar Solvent

The anhydrous gel deodorant composition of the present invention comprises one or more polar solvents having a selectively high solubility parameter. The concentration of the polar solvent in the anhydrous gel deodorant gel composition will vary with the specific combination of polar solvent, gellant, and optional other solvents in the composition, but must not exceed about 15% by weight of the composition, preferably from about 0.5% to about 10%, more preferably from about 1% to about 8%, even more preferably from about 3% to about 7%, by weight of the anhydrous gel deodorant composition, wherein the polar solvent has a solubility parameter of at least 12.5 $(cal/cm^3)^{0.5}$, preferably from 12.5 $(cal/cm^3)^{0.5}$ to about 25 $(cal/cm^3)^{0.5}$, more preferably from 12.5 $(cal/cm^3)^{0.5}$.

Nonlimiting examples of suitable polar solvents for use in the anhydrous gel deodorant composition include monohydric alcohols, polyhydric alcohols, and combinations thereof, examples of which include C1 to C20 monohydric alcohols, preferably C2 to C8 monohydric alcohols, and polypropylene glycols and polyethylene glycols having from 2 to 7 repeating ethoxylate or propoxylate groups, and polyglycerols having from 2 to 16 repeating glycerol moieties.

Specific examples of polar solvents suitable for use in the anhydrous gel deodorant composition include, but are not limited to, glycerin, propylene glycol, dipropylene glycol, ethanol, water, tripropylene glycol, butylene glycol, propylene glycol methyl ether, dipropylene glycol methyl ether, and combinations thereof. Most preferred is glycerin.

The gel deodorant compositions of the present invention are preferably substantially free of propylene glycol, dipropylene glycol, or combinations thereof. In this context, the term "substantially free" means that the compositions preferably contain less than 20%, more preferably less than 10%, most preferably zero percent, by weight of propylene glycol, dipropylene glycol, or combinations thereof.

A preferred embodiment of the anhydrous gel deodorant composition of the present invention are those which comprise glycerin as the polar solvent and a metal salt of a fatty acid as defined herein as the gellant, wherein the weight ratio of the glycerin to fatty acid salt is from about 0.5:1 to about 3:1, preferably from about 0.8:1 to about 1.5:1. It has been found that this narrow ratio of glycerin to fatty acid salt in the anhydrous gel deodorant composition allows for the formulation of a sufficiently hard gel stick which can also be formulated or processed using sufficiently low process temperatures to minimize or eliminate thermal degradation of heat sensitive materials in the composition. Most preferred are combinations of sodium stearate and glycerin.

Another embodiment of the anhydrous gel deodorant composition of the present invention are those which comprise a fatty acid or hydroxy fatty acid gellant as described herein, in the anhydrous gel deodorant composition also described herein. Unlike all other embodiments of the anhydrous gel deodorant compositions of the present invention, these compositions may contain but do not require the use of polar solvents and preferably contain less than 5%, more preferably less than 2%, even more preferably less than 0.1%, by weight of such polar solvents.

Other nonlimiting examples of polar solvents which may be suitable for use herein are described in U.S. Pat. No. 5,429,816; Cosmetics, Science, and Technology, Vol. 1, 27–104, edited by Balsam and Sagarin (1972); U.S. Pat. No. 4,202,879; and U.S. Pat. No. 4,816,261, which descriptions are incorporated herein by reference Moderately Polar Solvent The anhydrous gel deodorant composition of the present invention may further comprise one or more moderately polar solvents having a selectively moderate solubility parameter. This optional solvent is used in the anhydrous gel deodorant composition in addition to and in combination with the polar solvent described hereinbefore. The moderately polar solvent helps reduce syneresis of the anhydrous gel deodorant composition during shipping or prolonged storage, especially when such shipping or storage takes place in warmer climates or under warmer storage conditions. The moderately polar solvent also helps reduce process temperatures which can cause thermal degradation of fragrances or other similar materials in the anhydrous gel deodorant composition.

The moderately polar solvent comprises one or more solvents having a solubility parameter of from about 8.0 $(cal/cm^3)^{0.5}$ to less than 12.5 $(cal/cm^3)^{0.5}$, preferably from about 9.0 to less than 12.5 $(cal/cm^3)^{0.5}$, wherein the concentration of the moderately polar solvent in the anhydrous gel deodorant composition preferably ranges from about 0.1% to about 40%, more preferably from about 5% to about 30%. Selection of specific concentrations for a moderately polar solvent will vary depending on the other selected solvents and gellants in the anhydrous gel deodorant composition.

Nonlimiting examples of moderately polar solvents suitable for use in the anhydrous gel deodorant composition include ethoxylated ethers of fatty alcohols having from about 8 to about 30 carbon atoms, esters of polyhydric alcohols, esters of fatty acids, polyethylene glycols having at least 8 ethoxylate groups, polypropylene glycols having at least 8 propoxylate groups, nonpolymeric diols having at least 4 carbon atoms, and combinations thereof.

Specific nonlimiting examples of moderately polar solvents suitable for use in the gel deodorant composition include propyleneglycol monoisostearate; PPG-3 myristyl ether; PEG-8; hexylene glycol; 1,2, hexanediol; 1,2, PPG-14 butylether, dimethyl isosorbide, and combinations thereof. Preferred are hexylene glycol, PPG-3 myristyl ether, propyleneglycol monoisostearate, 1,2-hexanediol, and combinations thereof. It has been found that anhydrous gel deodorant compositions containing 1,2-hexanediol are especially effective in providing improved product clarity, and improved mildness when applied topically to the skin.

Optional Ingredients

The anhydrous gel deodorant compositions of the present invention may further comprise one or more optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants or other personal care compositions, and may also be used in the anhydrous gel deodorant compositions herein, provided that such optional materials are compatible with the essential materials described herein, or do not otherwise unduly impair product performance.

Nonlimiting examples of optional ingredients suitable for use in the anhydrous gel deodorant composition herein include pH buffering agents; additional emollients; humectants; soothing agents; dyes and pigments; medicaments; preservatives; and soothing agents such as aloe vera, allantoin, D-panthenol, avocado oil and other vegetative oils, and lichen extract.

Method of Manufacture

The compositions of the present invention may be made by any of the methods known in the art for formulating deodorant gel compositions. As will be apparent to those skilled in the art, the particular method will be dependent upon the selection of the specific types and amounts of the components employed.

In general, the compositions of the present invention can be prepared by mixing the polar solvent, volatile nonpolar solvent, deodorant active and any other optional solvents. Add gellant with agitation and heat the mixture to a temperature of from about 75° C. to about 100° C. to allow the gellant to melt and form a substantially clear or translucent liquid. The resulting solution is cooled before adding fragrance (if applicable), and then the cooled composition is poured into an appropriate container or dispenser at about 70° C. and allowed to solidify within the container or dispenser by cooling or allowing to cool the contained composition to ambient temperature.

Method For Use

The anhydrous gel deodorant composition of the present invention may be topically applied to the skin in any known or otherwise effective method for controlling malodor associated with perspiration. These methods comprise applying to the underarm or other area of the human skin of a safe and effective amount of the anhydrous gel deodorant composition of the present invention. In this context, the term "safe and effective amount" means an amount of the anhydrous gel deodorant composition topically applied to the skin which is effective in masking, reducing or eliminating malodor associated with human perspiration while being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or two times daily, preferably once daily.

EXAMPLES

The following examples illustrate specific embodiments of the anhydrous gel deodorant compositions of the present invention, including methods of manufacture and use, but are not intended to be limiting thereof. Other modifications can be undertaken by the skilled artisan without departing from the spirit and scope of this invention.

Each of the exemplified compositions are prepared by combining all of the listed components, except for the gellant and fragrance where applicable, and heating with agitation the combination of ingredients to a temperature above the melt point of the gellant but less than 110° C. The gellant is then added while continuing to heat and agitate the mixture until a substantially clear or translucent liquid results, at which point the liquid is cooled to a temperature of between 69° C. and 73° C. Fragrance is added with agitation to the cooled liquid. The fragrance-containing liquid is then poured into an appropriate dispenser or other container and allowed to solidify by cooling to ambient temperature.

TABLE 1

| Ingredient | Examples | | | | |
|---|---|---|---|---|---|
|  | 1 | 2 | 3 | 4 | 5 |
| Isopar V | 7 | 30 | — | — | — |
| Isopar M | 40.45 | 5 | — | 18.1 | 41.5 |
| Isopar L | — | — | 18.1 | — | — |
| Permethyl 99A | — | — | 27.75 | — | — |

TABLE 1-continued

| Ingredient | Examples | | | | |
|---|---|---|---|---|---|
|  | 1 | 2 | 3 | 4 | 5 |
| Butyl stearate | — | 25 | 14.75 | 17 | 30 |
| Polydimethyl siloxane 50 centistokes (cs) | — | — | 12 | 12 | — |
| Propylene glycol monoisostearate | 3.5 | 16 | 7 | 6.5 |  |
| PPG-3 myristryl ether | 3.5 | — | — | 0.6 | — |
| Mineral oil | 15 | — | — | — | — |
| Hexyleneglycol | 12.75 | 15 | 10 | 16.75 | — |
| glycerin | 2.5 | 3 | 3 | 3.35 | — |
| Propylene glycol | — | — | — | — | 0.5 |
| Ethanol | 6 | — | — | — | — |
| Fragrance | 5.5 | 2.5 | 3.5 | 3.4 | 3 |
| Triclosan | 0.3 | 0.3 | 0.3 | 0.3 | 0.3 |
| Sodium stearate | 3.5 | 3.2 | 3.7 | 3.9 | — |
| 12-HSA | — | — | — | — | 10 |
| Cyclomethicone | — | — | — | — | 14.7 |
| Disopropyl adipate | — | — | 18 | — | — |

TABLE 2

| Ingredients | Examples | | | |
|---|---|---|---|---|
|  | 6 | 7 | 8 | 9 |
| Isopar V | 7 | 30 | — | — |
| Isopar M | 40.45 | 5 | — | 18.1 |
| Isopar L | — | — | — | 18.1 |
| Permethyl 99A | — | — | 27.75 | — |
| Butyl stearate | — | 25 | 14.75 | 17 |
| Polydimethyl siloxane 50 centistokes (cs) | — | — | 12 | 12 |
| Propylene glycol monoisostearate | 3.5 | 16 | 7 | 6.5 |
| PPG-3 myristryl ether | 3.5 | — | — | 0.6 |
| Mineral oil | 15 | — | — | — |
| 1,2-hexanediol | 12.75 | 15 | 10 | 16.75 |
| glycerin | 2.5 | 3 | 3 | 3.35 |
| Ethanol | 6 | — | — | — |
| Fragrance | 5.5 | 2.5 | 3.5 | 3.4 |
| Triclosan | 0.3 | 0.3 | 0.3 | 0.3 |
| Sodium stearate | 3.5 | 3.2 | 3.7 | 3.9 |
| Disopropyl adipate | — | — | 18 | — |

TABLE 3

| Ingredient | Examples | | | | | |
|---|---|---|---|---|---|---|
|  | 10 | 11 | 12 | 13 | 14 | 15 |
| Isopar V | 7 | 29.75 | — | — | — | — |
| Isopar M | 40.20 | 5 | — | 18.1 | 41.5 | 11.5 |
| Isopar L | — | — | — | 18.1 | — | 11.5 |
| Permethyl 99A | — | — | 27.50 | — | — | — |
| Butyl stearate | — | 25 | 14.75 | 16.75 | 29.75 | 15.9 |
| Polydimethyl siloxane 50 50 centistokes (cs) | — | — | 12 | 12 | — | — |
| Propylene glycol mono-isostearate | 3.5 | 16 | 7 | 6.5 | — | 22.0 |
| PPG-3 myristryl ether | 3.5 | — | — | 0.6 | — | — |
| Mineral oil | 15 | — | — | — | — | — |
| Tripropylene glycol | — | — | — | — | — | 25.0 |
| 1,2-hexanediol | 12.75 | 15 | 10 | 16.75 | — | — |
| glycerin | 2.5 | 3 | 3 | 3.35 | — | 3.8 |
| Propylene glycol | — | — | — | — | 0.5 | — |
| Ethanol | 6 | — | — | — | — | — |
| Fragrance | 5.5 | 2.5 | 3.5 | 3.4 | 3 | 3.5 |
| Triclocaxban | 0.25 | 0.25 | 0.25 | 0.25 | 0.25 | 0.25 |
| Triclosan | 0.3 | 0.3 | 0.3 | 0.3 | 0.3 | 0.3 |
| Sodium stearate | 3.5 | 3.2 | 3.7 | 3.9 | — | 5.5 |
| 12-HSA | — | — | — | — | 10 | — |
| Cyclomethicone | — | — | — | — | 14.7 | — |

TABLE 3-continued

| Ingredient | Examples | | | | | |
|---|---|---|---|---|---|---|
| | 10 | 11 | 12 | 13 | 14 | 15 |
| Disopropyl adipate | — | — | 18 | — | — | — |
| Tween 20 | — | — | — | — | — | 0.75 |

TABLE 4

| Ingredient | Examples | | | | |
|---|---|---|---|---|---|
| | 16 | 17 | 18 | 19 | 20 |
| Trimellitate (Jayflex TINTM) | 60 | — | — | 24 | 25 |
| Octylmethoxyl Cinnamate | — | 25 | — | 32.5 | — |
| Isopar L | 32.5 | — | — | 32.5 | — |
| Permethyl 101A | — | 40 | — | — | 40 |
| Permethyl 104A | — | — | 47 | — | — |
| Mineral Oil | — | — | 47 | — | 25 |
| Petrolatum | — | — | — | 5 | — |
| Cyclomethicone D-5 | 4 | 25 | — | — | — |
| Propylene Carbonate | — | — | — | 0.3 | 0.3 |
| Bentone 27 | — | — | — | 1 | — |
| Stearyl Alcohol | — | — | — | — | 2 |
| 12-HSA | — | 8 | 5 | 2 | 5 |
| Fragrance | 3.5 | 2 | 1 | 2.7 | 2.7 |

The resulting compositions described in Tables 1–4 are gel deodorants which are then applied topically to the underarm in an amount ranging from about 0.1 gram to about 2 grams per axilla The applied compositions are effective in reducing, masking or eliminating perspiration odor, and have good skin feel characteristics during and after application. The applied compositions are mild to the skin and cause little or no skin irritation. All exemplified amounts are weight-weight percents based on the total weight of the composition, unless otherwise specified.

What is claimed is:

1. An anhydrous gel deodorant composition comprising:
   (a) from about 0.001% to about 50% by weight of deodorant active, fragrance, or combination thereof;
   (b) from about 0.01% to about 20% by weight of a gellant;
   (c) from about 1% to about 50% by weight of a nonpolar volatile solvent having a solubility parameter of less than 8.0 $(cal/cm^3)^{0.5}$, a vapor pressure of from about 0.01 mm Hg to about 6 mm Hg at 25° C., and an average boiling point of less than about 250° C.; and
   (d) from about 1% to about 15% by weight of a polar solvent having a solubility parameter of from 12.5 to about 25 $(cal/cm^3)^{0.5}$.

2. The anhydrous gel deodorant composition of claim 1 wherein the composition contains less than about 1% by weight of water, and wherein the gellant is a fatty acid alkali metal salt having from about 12 to about 22 carbon atoms.

3. The anhydrous gel deodorant composition of claim 2 wherein the fatty acid salt is selected from the group consisting of sodium stearate, sodium palmitate, potassium stearate, sodium behenate, sodium arachidate, sodium laurate, potassium palmitate, sodium myristate, and combinations thereof.

4. The anhydrous gel deodorant composition of claim 3 wherein the fatty acid salt comprises sodium stearate.

5. The anhydrous gel deodorant composition of claim 1 wherein the nonpolar volatile solvent is a volatile branched chain hydrocarbon having from about 4 to about 40 carbon atoms.

6. The anhydrous gel deodorant composition of claim 5 wherein the volatile branched chain hydrocarbon has a solubility parameter of from about 5 $(cal/cm^3)^{0.5}$ to less than 8.0 $(cal/cm^3)^{0.5}$ and a vapor pressure of from about 0.01 mmHg to about 1.5 mmHg at 25° C.

7. The anhydrous gel deodorant composition of claim 6 wherein the composition comprises a combination of two or more volatile branched chain hydrocarbons having different molecular weights, each of which also has from about 6 to about 20 carbon atoms.

8. The anhydrous gel deodorant composition of claim 7 wherein the volatile branched chain hydrocarbon is selected from the group consisting of C13–C14 isoparaffin, C7–C8 Isoparaffin, C8–C9 Isoparaffin, C10–11 Isoparaffin, $C_{11}$–C13 Isoparaffin, C11–C12 Isoparaffin, and combinations thereof.

9. The composition of claim 2 wherein the polar solvent is selected from the group consisting of glycerin, propylene glycol, dipropylene glycol, ethanol, tripropylene glycol, butylene glycol, propylene glycol methyl ether, dipropylene glycol methyl ether, and combinations thereof.

10. The anhydrous gel deodorant composition of claim 9 wherein the polar solvent comprises glycerin, the fatty acid salt is sodium stearate, and the weight ratio of glycerin to sodium stearate is from about 0.8:1 to about 1.5:1.

11. The anhydrous gel deodorant composition of claim 2 wherein the composition contains less than about 5% by weight of aromatic hydrocarbons selected from the group consisting of α-pinene, β-pinene, d-limonene and other terpenes.

12. The anhydrous gel deodorant composition of claim 2 wherein the deodorant active is selected from the group consisting of triclocarban, triclosan, and combinations thereof.

13. The anhydrous gel deodorant composition of claim 12 wherein the composition comprises from about 0.01% to about 1.0% by weight of triclosan and from about 0.01% to about 1.0% by weight of triclocarban.

14. The anhydrous gel deodorant composition of claim 2 wherein the composition further comprises from about 0.1% to about 40% by weight of a moderately polar solvent having a solubility parameter of from 8.0 $(cal/cm^3)^{0.5}$ to less than 12.5 $(cal/cm^3)^{0.5}$.

15. The anhydrous gel deodorant composition of claim 14 wherein the moderately polar solvent comprises 1,2-hexanediol.

16. An anhydrous deodorant composition comprising:
   (a) from about 0.001% to about 50% by weight of deodorant active, fragrance, or combination thereof;
   (b) from about 0.01% to about 20% by weight of a gellant selected from the group consisting of fatty acids, hydroxy fatty acids, and combinations thereof; and
   (c) from about 1% to about 50% by weight of a nonpolar volatile solvent having a solubility parameter of less than 8.0 $(cal/cm^3)^{0.5}$, a vapor pressure of from about 0.01 mm Hg to about 6 mm Hg at 25° C., and an average boiling point of less than about 250° C.

17. The anhydrous gel deodorant composition of claim 16 wherein the composition contains less than 1% by weight of water, and the gellant has from about 12 to about 40 carbon atoms.

18. The anhydrous gel deodorant composition of claim 17 wherein the nonpolar volatile solvent is a volatile branched chain hydrocarbon having from about 4 to about 40 carbon atoms.

19. The anhydrous gel deodorant composition of claim 18 wherein the volatile branched chain hydrocarbon has a solubility parameter of from about 5 $(cal/cm^3)^{0.5}$ to less than 8.0 $(cal/cm^3)^{0.5}$ and a vapor pressure of from about 0.01 mmHg to about 1.5 mmHg at 25° C.

20. The anhydrous gel deodorant composition of claim 19 wherein the composition comprises a combination of two or more volatile branched chain hydrocarbons having different molecular weights, each of which also has from about 6 to about 20 carbon atoms.

21. The anhydrous gel deodorant composition of claim 20 wherein the volatile branched chain hydrocarbon is selected from the group consisting of C13–C14 isoparaffin, C7–C8 Isoparaffin, C8–C9 Isoparaffin, C10–11 Isoparaffin, C11–C13 Isoparaffin, C11–C12 Isoparaffin, and combinations thereof.

22. The anhydrous gel deodorant composition of claim 2 wherein the composition contains less than about 5% by weight of aromatic hydrocarbons selected from the group consisting of α-pinene, β-pinene, d-limonene and other terpenes.

23. The anhydrous gel deodorant composition of claim 2 wherein the deodorant active is selected from the group consisting of triclocarban, triclosan, and combinations thereof.

24. The anhydrous gel deodorant composition of claim 23 wherein the composition comprises from about 0.01% to about 1.0% by weight of triclosan and from about 0.01% to about 1.0% by weight of triclocarban.

25. The anhydrous gel deodorant composition of claim 2 wherein the composition further comprises 1,2-hexanediol.

26. The anhydrous gel deodorant composition of claim 17 wherein the gellant is a fatty acid selected from the group consisting of 12-hydroxystearic acid, 12-hydroxylauric acid, 16-hydroxyhexadecanoic acid, behenic acid, eurcic acid, stearic acid, caprylic acid, lauric acid, isostearic acid, and mixtures thereof.

* * * * *